(12) United States Patent
Endo et al.

(10) Patent No.: US 10,966,929 B2
(45) Date of Patent: Apr. 6, 2021

(54) FREEZE-DRIED ALGINIC ACID PREPARATION

(71) Applicant: MOCHIDA PHARMACEUTICAL CO., LTD., Tokyo (JP)

(72) Inventors: Shuichi Endo, Fujieda (JP); Naoya Yoshioka, Fujieda (JP)

(73) Assignee: MOCHIDA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 15/757,766

(22) PCT Filed: Sep. 6, 2016

(86) PCT No.: PCT/JP2016/076176
§ 371 (c)(1),
(2) Date: Mar. 6, 2018

(87) PCT Pub. No.: WO2017/043485
PCT Pub. Date: Mar. 16, 2017

(65) Prior Publication Data
US 2018/0338921 A1    Nov. 29, 2018

(30) Foreign Application Priority Data
Sep. 7, 2015 (JP) .............................. JP2015-175583

(51) Int. Cl.
| A61K 9/19 | (2006.01) |
| A61K 47/02 | (2006.01) |
| A61K 31/734 | (2006.01) |
| A61K 47/36 | (2006.01) |
| A61L 27/00 | (2006.01) |

(52) U.S. Cl.
CPC .............. *A61K 9/19* (2013.01); *A61K 31/734* (2013.01); *A61K 47/02* (2013.01); *A61K 47/36* (2013.01); *A61L 27/00* (2013.01)

(58) Field of Classification Search
CPC ......... A61K 9/19; A61K 31/734; A61K 47/02
See application file for complete search history.

(56) References Cited

U.S. PATENT DOCUMENTS

| 5,718,916 A | 2/1998 | Scherr |
| 7,378,408 B2 | 5/2008 | Kimball et al. |
| 8,648,177 B2 | 2/2014 | Guo et al. |
| 2006/0240080 A1 | 10/2006 | Han et al. |
| 2009/0208492 A1 | 8/2009 | O'Connor et al. |
| 2010/0015102 A1 | 1/2010 | Iwasaki et al. |
| 2010/0082102 A1* | 4/2010 | Govil .............. A61L 27/54 623/11.11 |
| 2010/0136140 A1* | 6/2010 | Zhao .............. A61K 31/047 424/680 |
| 2011/0053886 A1 | 3/2011 | Melvik et al. |
| 2012/0277859 A1 | 11/2012 | Govil et al. |
| 2013/0189231 A1* | 7/2013 | Iwasaki .............. A61L 27/20 424/93.7 |
| 2014/0239528 A1 | 8/2014 | Govil et al. |
| 2016/0206562 A1 | 7/2016 | Kuwata |
| 2017/0348236 A1 | 12/2017 | Kuwata |

FOREIGN PATENT DOCUMENTS

| CN | 102159255 A | 8/2011 | |
| CN | 10343638 A | 12/2013 | |
| EP | 0 227 553 A2 | 12/1986 | |
| JP | 6-343479 A | 12/1994 | |
| JP | 2005/75815 A | 3/2005 | |
| JP | 2005/145885 A | 6/2005 | |
| JP | 2005145885 * | 6/2005 | ............... C07H 3/06 |
| JP | 2012-503498 A | 2/2012 | |
| WO | WO 2008/102855 A1 | 8/2008 | |
| WO | WO 2010/039184 A2 | 4/2010 | |
| WO | WO 2015/025979 A1 | 2/2015 | |

OTHER PUBLICATIONS

English translation of International Preliminary Report on Patentability and Written Opinion dated Mar. 22, 2018, in PCT International Application No. PCT/JP2016/076176.
FMC Biopolymer, Pronova™ sodium alginates catalogue, 2002, 3 pages.
International Search Report, issued in PCT/JP2016/076176, dated Oct. 25, 2016.
Sato et al., "On the Improvements in Manufacturing of Algninic Acid (4) Study on Viscosity Deterioration of Sodium Alginate Owing to Heating", Muroran Institute of Technology Research Report, 1957, vol. 2, No. 3, pp. 609-616.
Sato et al., "On the Improvements in Manufacturing of Alginic Acid (6) Study of Viscosity Deterioration of Free Alginic Acid by Heating", Muroran Institute of Technology Research Report, 1960, vol. 3, pp. 443-449.
Written Opinion of the International Searching Authority, issued in PCT/JP2016/076176, dated Oct. 25, 2016.
Yomota et al., "Evaluation of Molecular Weight of Hyaluronate Preparations by Size-exclusion Chromatography", Bull. Natl. Health Sci., 1999, vol. 117, pp. 135-139.

(Continued)

*Primary Examiner* — Pancham Bakshi
(74) *Attorney, Agent, or Firm* — Birch, Stewart, Kolasch & Birch, LLP

(57) ABSTRACT

The present invention provides: a freeze-dried composition which comprises (a) a monovalent metal alginate and (b) a salt selected from a monovalent metal salt and an ammonium salt; and a method of producing a freeze-dried monovalent metal alginate composition which comprises the steps of freezing an aqueous solution formed by dissolving at least the component (a) and the component (b), performing first drying, and then performing second drying as desired to reduce a water content to 3% by mass or less. This is a freeze-dried monovalent metal alginate composition with suppressed viscosity decrease with the lapse of time.

21 Claims, 1 Drawing Sheet

(56) References Cited

OTHER PUBLICATIONS

Yomota, "Evaluation of Molecular Weights of Hyaluronate Preparations by Multi-Angle Laser Light Scattering", Bull. Natl. Inst. Health Sci., 2003, vol. 121, pp. 30-33.
Extended European Search Report dated Jul. 23, 2018 in Patent Application No. 16844346.3.
Chinese Office Action and Search Report, dated Dec. 3, 2019 (received on Jan. 6, 2020) for Chinese Application No. 201680051699.1, with an English translation of the Chinese Office Action.
Russian Office Action and Search Report for Russian Application No. 2018112431, dated Feb. 13, 2020, with English translation.
Aida et al., "Pressure Enhanced Self Catalytic Decomposition of Alginic Acid in High Temperature High Pressure Water," Grants-in-Aid for Scientific Research (Scientific Research Fund): Research Report, Form C-19, Japan, May 16, 2012, 9 pages, with a partial English translation.
Japanese Office Action, dated Aug. 3, 2020, for Japanese Application No. 2017-539172, with an English machine translation.

* cited by examiner

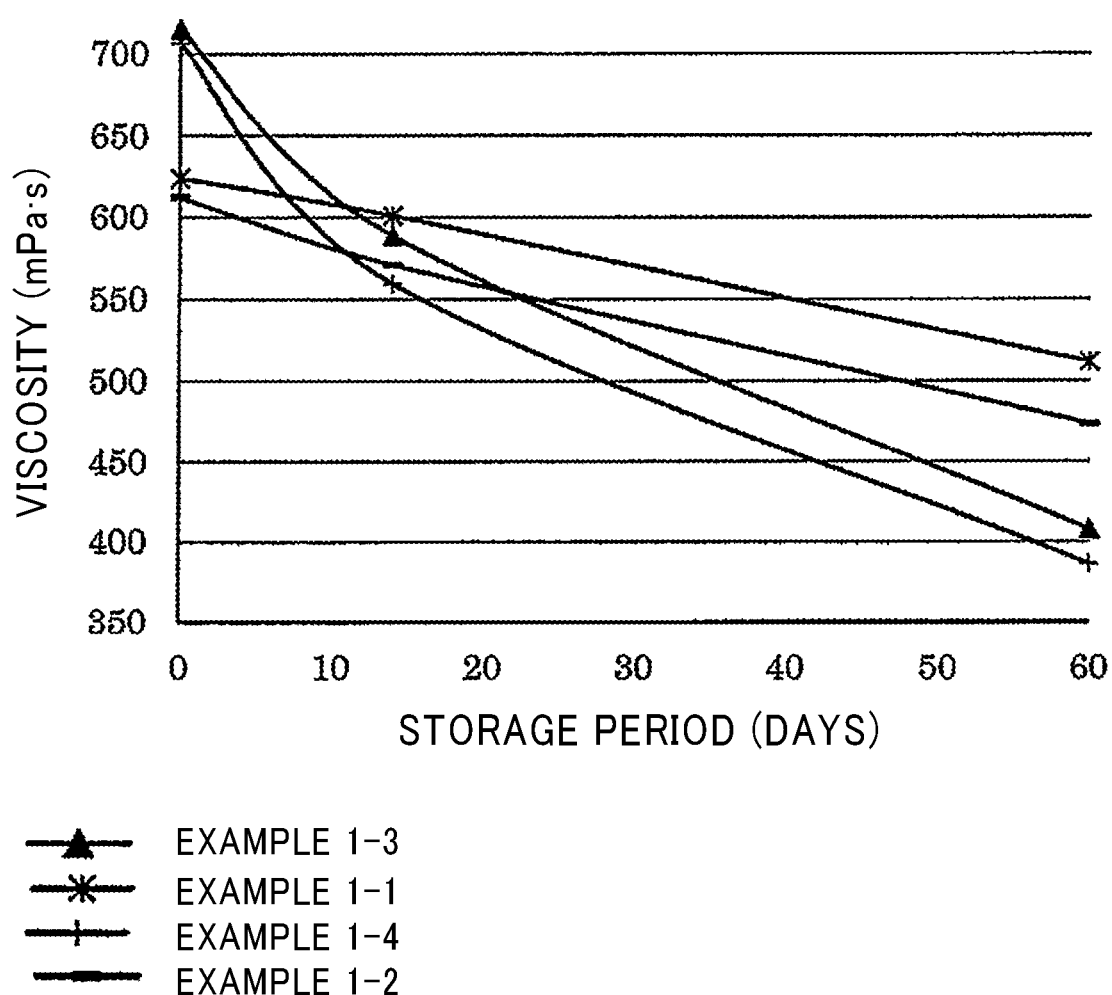

FREEZE-DRIED ALGINIC ACID PREPARATION

TECHNICAL FIELD

The present invention relates to a freeze-dried monovalent metal alginate preparation (for which the term "composition" is used representatively including a freeze-dried body, a freeze-dried material, and a freeze-dried composition as well as the freeze-dried preparation) which is useful as, for example, pharmaceuticals such as a composition for cartilage regeneration, a cartilage disorder therapeutic agent, and an antiadhesive material, a medical material, medical equipment, and a reagent, and in particular to a freeze-dried monovalent metal alginate composition with suppressed viscosity decrease with the lapse of time, an in-vial freeze-dried composition, a method of producing the same, a suppressant of viscosity decrease with the lapse of time for a freeze-dried monovalent metal alginate composition, a method of suppressing viscosity decrease with the lapse of time of a freeze-dried monovalent metal alginate composition, and a method of stabilizing a freeze-dried monovalent metal alginate composition, especially a storage-stabilizing method.

BACKGROUND ART

It is known to inject a cartilage defect portion in an articular cartilage with an aqueous solution formed by dissolving a freeze-dried monovalent metal alginate composition such as a freeze-dried sodium alginate composition in water, thereby regenerating and treating the cartilage (Patent Literature 1).

Meanwhile, industrial sodium alginate contains sodium chloride, sodium sulfate, sodium hydroxide, sodium carbonate, and the like as impurity electrolytes. It has been investigated that the impurity electrolytes can be removed using a property of being extracted by an alcohol of about 40% or more and that properties such as viscosity, pH, structural viscosity, flow curve, and capillary action in the case of adding sodium chloride or sodium sulfate to the sodium alginate aqueous solution change (Non Patent Literatures 1 and 2).

In addition, a study was carried out on the viscosity decrease attributed to the heating of sodium alginate in the forms of powder and solution. As a result, it has been reported that although viscosity decreases due to heating in both cases, the solution form has a larger viscosity decrease rate (Non Patent Literatures 3 and 4).

However, it is not known so far that if a freeze-dried monovalent metal alginate composition is kept in storage, there arises a problem that the monovalent metal alginate in the freeze-dried composition is deteriorated over time and the viscosity decreases.

CITATION LIST

Patent Literature

Patent Literature 1: International Publication No. WO 2008/102855

Non Patent Literatures

Non Patent Literature 1: Kagaku Kogyo Magazine vol. 61, No. 7, 1958 pp. 871-874

Non Patent Literature 2: Kagaku Kogyo Magazine vol. 61, No. 7, 1958 pp. 874-877

Non Patent Literature 3: Muroran Institute of Technology Research Report, 1957, Vol. 2, No. 3, pp. 609-616

Non Patent Literature 4: Muroran Institute of Technology Research Report, 1960, Vol. 3, pp. 443-449

SUMMARY OF INVENTION

Problems to be Solved by the Invention

The present invention aims to provide a freeze-dried monovalent metal alginate composition with improved stability, and in particular aims to provide a freeze-dried composition whose long-term storage stability is improved. Furthermore, the present invention aims to provide a highly pure freeze-dried monovalent metal alginate composition which does not substantially contain an endotoxin.

The present invention aims to provide a freeze-dried monovalent metal alginate composition with suppressed viscosity decrease with the lapse of time in a freeze-dried state.

The present invention aims to provide an in-vial freeze-dried monovalent metal alginate composition with suppressed viscosity decrease with the lapse of time.

The present invention aims to provide a method of efficiently producing a freeze-dried monovalent metal alginate composition with suppressed viscosity decrease with the lapse of time.

The present invention aims to provide a suppressant of viscosity decrease with the lapse of time for a freeze-dried monovalent metal alginate composition which includes an active ingredient being a salt selected from a monovalent metal salt and an ammonium salt.

The present invention aims to provide a method of suppressing viscosity decrease with the lapse of time of a freeze-dried monovalent metal alginate composition which includes adding a salt selected from a monovalent metal salt and an ammonium salt prior to freeze-drying.

Means for Solution of the Problems

The present inventors have made earnest studies and as a result completed the present invention based on the surprising knowledge that it is possible to efficiently suppress viscosity decrease with the lapse of time of a monovalent metal alginate in a freeze-dried monovalent metal alginate composition by using a freeze-dried aqueous solution formed by dissolving (a) a monovalent metal alginate and (b) a salt selected from a monovalent metal salt and an ammonium salt.

To be more specific, the present invention has the following aspects.

(1-1) A freeze-dried composition comprising (a) a monovalent metal alginate and (b) a salt selected from a monovalent metal salt and an ammonium salt.

(1-2) The freeze-dried composition according to (1-1) described above which is a freeze-dried aqueous solution formed by dissolving at least the components (a) and (b).

(1-3) The freeze-dried composition according to (1-1) or (1-2) described above, in which a water content is 3% by mass or less.

(1-4) The freeze-dried composition according to any one of (1-1) to (1-3) described above, in which a mass ratio of the component (a)/the component (b) is 100/70 to 100/10.

(1-5) The freeze-dried composition according to any one of (1-1) to (1-4) described above, in which the component (b)

is at least one selected from the group consisting of sodium chloride and potassium chloride.

(1-6) The freeze-dried composition according to any one of (1-1) to (1-5) described above, consisting of the component (a) and the component (b).

(1-7) The freeze-dried composition according to any one of (1-1) to (1-6) described above, in which the component (a) is a highly pure monovalent metal alginate not substantially containing an endotoxin.

(2-1) An in-vial freeze-dried composition formed by storing the freeze-dried composition according to any one of (1-1) to (1-7) described above.

(2-2) The in-vial freeze-dried composition according to (2-1) described above, in which a volume of a vial is 2 to 50 ml.

(2-3) The in-vial freeze-dried composition according to (2-1) or (2-2) described above, in which air in the vial is substituted with nitrogen gas.

(3-1) A method of producing a freeze-dried composition, comprising freeze-drying an aqueous solution formed by dissolving at least (a) a monovalent metal alginate and (b) a salt selected from a monovalent metal salt and an ammonium salt.

(3-2) The production method according to (3-1) described above, comprising the step of freezing an aqueous solution formed by dissolving at least the component (a) and the component (b), performing first drying under reduced pressure within a temperature range where the freezing is kept, and then performing second drying to reduce a water content to 3% by mass or less.

(3-3) The production method according to (3-2) described above, comprising performing the second drying under the same temperature condition as the first drying or under a temperature condition higher than a temperature of the first drying.

(3-4) The production method according to any one of (3-1) to (3-3) described above, comprising filling a vial with the aqueous solution formed by dissolving at least the component (a) and the component (b) and then performing freeze-drying.

(4-1) A suppressant of viscosity decrease with the lapse of time for a freeze-dried monovalent metal alginate composition, comprising an active ingredient being a salt selected from a monovalent metal salt and an ammonium salt.

(5-1) A method of suppressing viscosity decrease with the lapse of time of a freeze-dried monovalent metal alginate composition, comprising causing the freeze-dried monovalent metal alginate composition to contain a salt selected from a monovalent metal salt and an ammonium salt.

The present invention improves the stability of a freeze-dried monovalent metal alginate composition represented by, for example, sodium alginate. In addition, the present invention makes it possible to provide a freeze-dried monovalent metal alginate composition which can efficiently suppress viscosity decrease with the lapse of time of a monovalent metal alginate in a freeze-dried monovalent metal alginate composition even in the case of long-term storage or preservation. Further, the present invention provides a method of producing a freeze-dried monovalent metal alginate composition which comprises the step of freezing an aqueous solution containing the component (a) and the component (b), performing first drying under reduced pressure within a temperature range where the freezing is kept, and then performing second drying to reduce a water content to 3% by mass or less, in which the second drying can be performed under a temperature condition higher than the temperature of the first drying. Hence, the present invention has an advantage of being able to shorten the production time.

BRIEF DESCRIPTION OF DRAWINGS

FIG. 1 is a diagram showing how viscosity decreases over time for freeze-dried sodium alginate compositions not added with sodium chloride [Examples 1-3 and 1-4] and freeze-dried sodium alginate compositions added with sodium chloride [Examples 1-1 and 1-2].

DESCRIPTION OF EMBODIMENT

Alginic acid, which is a constituent component of a monovalent metal alginate (a) used in the present invention, is a natural polysaccharide which is produced by extraction from seaweed followed by purification. In addition, alginic acid is a polymer formed by polymerization of D-mannuronic acid (M) and L-guluronic acid (G). The constituent ratio (M/G ratio) between D-mannuronic acid and L-guluronic acid of alginic acid differs depending mainly on the type of creature such as seaweed from which alginic acid is derived and is also affected by the habitat of the creature and by seasons. The M/G ratio is wide in range, where the high-G type has an M/G ratio of about 0.4 and the high-M type has an M/G ratio of about 5. Alginic acid has varying physicochemical properties depending on the M/G ratio of alginic acid, the arrangement of M and G, and the like. In addition, the preferable use can differ. A method of industrially producing alginic acid includes, for example, the alginic acid method and the calcium alginate method. In the present invention, it is possible to use alginic acid produced by any of these methods. The quantitative value determined by purification and the HPLC method is preferably within a range of 80 to 120% by mass, more preferably within a range of 90 to 110% by mass, and further preferably within a range of 95 to 105% by mass. In the present invention, one having a quantitative value determined by the HPLC method within the ranges described above is referred to as high purity alginic acid. The alginic acid used in the present invention is preferably high purity alginic acid. Commercially available products that can be purchased and utilized include products marketed by KIMICA Corporation as KIMICA ALGIN series, preferably products of fine food & pharmaceutical grades. It is possible to use commercially available products after further purification as appropriate.

The monovalent metal alginate used in the present invention is preferably one in which the hydrogen cation of a carboxyl group of alginic acid is ion-exchanged with a monovalent metal cation such as sodium and potassium, particularly an alkali metal cation. Among these, sodium alginate, potassium alginate, a mixture of these, or the like is preferable, and sodium alginate is particularly preferable.

The monovalent metal alginate used in the present invention is recommended to be one having an appropriate weight average molecular weight depending on the end use purpose. For example, in the case of use for the treatment of cartilage disorder, the weight average molecular weight is preferably 500,000 to 5,000,000, more preferably 650,000 or more, and further preferably 800,000 or more and 3,000,000 or less.

Since the monovalent metal alginate is a polysaccharide, it is difficult to accurately determine the molecular weight. In general and in the present invention, it is possible to use a monovalent metal alginate having a weight average molecular weight of, for example, 5,000 or more and preferably 10,000 or more, and 10,000,000 or less and more preferably 5,000,000 or less.

In general, a polymer substance of natural origin does not have a single molecular weight. Since the polymer substance of natural origin is a collection of molecules having various molecular weights, it is measured as a molecular weight distribution having a certain width. A representative measuring method is gel filtration chromatography. The representative information on the molecular weight distribution obtained by gel filtration chromatography includes the weight average molecular weight (Mw), the number average molecular weight (Mn), and the dispersion ratio (Mw/Mn).

The weight average molecular weight places importance on the contribution of polymers having large molecular weights to the average molecular weight and is expressed by the following equation.

$$Mw=\Sigma(WiMi)/W=\Sigma(HiMi)/\Sigma(Hi)$$

The number average molecular weight is calculated by dividing the total weight of the polymer by the total number of the polymers:

$$Mn=W/\Sigma Ni=\Sigma(MiNi)/\Sigma Ni=\Sigma(Hi)/\Sigma(Hi/Mi),$$

where W is the total weight of the polymer, Wi is the weight of the i-th polymer, Mi is the molecular weight in the i-th elution time, Ni is the number of the molecular weights Mi, and Hi is the height in the i-th elution time.

It is known that in the molecular weight measurement of a polymer substance of natural origin, the values can differ depending on the measurement method (examples of hyaluronic acid: Chikako YOMOTA et. al. Bull. Natl. Health Sci., Vol. 117, pp 135-139 (1999), Chikako YOMOTA et. al. Bull. Natl. Inst. Health Sci., Vol. 121, pp 30-33 (2003)). Regarding the molecular weight measurement of an alginate, there is a literature (ASTM F2064-00 (2006), published by ASTM International) which describes a calculation method starting from intrinsic viscosity and a calculation method by SEC-MALLS (size exclusion chromatography with multiple angle laser light scattering detection). Note that when measuring the molecular weight by size exclusion chromatography (=gel filtration chromatography), this literature states that it is insufficient only to perform calculation with a calibration curve using pullulan as a standard substance and recommends to also use a multiple angle laser light scattering (MALLS) detector (=measurement by SEC-MALLS). In addition, there is a case where the molecular weight measured by SEC-MALLS is employed as a specification value for an alginate catalog (FMC Biopolymer, PRONOVA™ sodium alginates catalogue).

In the present specification, in the case of identifying the molecular weight of an alginate, the molecular weight in consideration is the weight average molecular weight calculated by gel filtration chromatography unless otherwise noted. Preferable conditions of gel filtration chromatography involve, for example, use of a calibration curve with pullulan as a standard substance. The molecular weight of pullulan used as a standard substance is preferably at least 1,600,000, 788,000, 404,000, 212,000, and 112,000. In addition to the above, it is possible to determine eluent (200 mM solution of sodium nitrate), column condition, and the like. As the column condition, it is preferable to use a polymethacrylate resin-based packing material and to use at least one column having an exclusion limit molecular weight of 10,000,000 or more. A representative column is TSKgel GMPWxl (diameter of 7.8 mm×300 mm) (manufactured by Tosoh Corporation).

In addition, the monovalent metal alginate used in the present invention is recommended to be one having an appropriate viscosity depending on the end use purpose. For example, in the case of use for the treatment of cartilage disorder, the viscosity of 1% liquid (20° C.) measured by the viscosity measuring method conforming to the Japanese Pharmacopoeia is preferably 50 to 20,000 mPa·s, more preferably 50 to 10,000 mPa·s, more preferably 100 to 5,000 mPa·s, more preferably 300 to 800 mPa·s, and further preferably 300 to 600 mPa·s.

In addition, the monovalent metal alginate used in the present invention is recommended to be one having an appropriate M/G ratio depending on the end use purpose. For example, in the case of use for the treatment of cartilage disorder, M/G ratio is preferably 0.4 to 2.0, more preferably 0.6 to 1.8, and further preferably 0.8 to 1.6.

In addition, the monovalent metal alginate used in the present invention is recommended to be one having a reduced endotoxin level. The endotoxin value measured by the endotoxin test conforming to the Japanese Pharmacopoeia is preferably less than 100 EU/g, more preferably less than 75 EU/g, and further preferably less than 50 EU/g. In the present invention, "substantially not containing an endotoxin" means that the endotoxin value measured by the endotoxin test conforming to the Japanese Pharmacopoeia is within the numerical ranges described above.

The monovalent metal salt and the ammonium salt used as the component (b) of the present invention include a water-soluble inorganic salt and a water-soluble organic salt. In particular, it is preferable to use the water-soluble inorganic salt. Among these, as the monovalent metal salt, it is preferable to use a salt of monovalent metal such as sodium and potassium, in particular a water-soluble salt of alkali metal. To be more specific, the inorganic salt includes, for example, a hydrochloride, a sulfate, and a nitrate of an alkali metal, and the organic salt includes, for example, a citrate, a tartrate, an acetate, a malate, and a succinate of an alkali metal. Among these, a hydrochloride is preferable, and sodium chloride and potassium chloride are particularly preferable. Sodium chloride is most preferable.

In addition, a preferable ammonium salt includes water-soluble ammonium chloride, ammonium acetate, and the like.

In the present invention, the mass ratio of the component (a)/the component (b) is preferably 100/70 to 100/10, more preferably 100/60 to 100/30, and most preferably 100/about 44. If the component (b) is sodium chloride, it is preferable to blend the component (a) with the component (b) so that the concentration is equivalent to that of physiological saline when supplied with injection water.

The freeze-dried composition of the present invention is preferably a freeze-dried aqueous solution containing the components (a) and (b). Here, the freeze-dried composition is one having a water content of preferably 3% by mass or less, in particular a water content of 2% by mass or less and further preferably 1% by mass or less.

The freeze-dried composition of the present invention can contain sugars such as mannitol, xylitol, and white soft sugar as long as the performance thereof is not impaired, but preferably contain only the component (a) and the component (b).

Consider the viscosity of a solution of the freeze-dried composition of the present invention which is supplied with injection water immediately after freeze-drying so that the concentration is adjusted to 1% by mass. In a freeze-dried sodium alginate composition not added with a salt, the viscosity usually indicates a value of 500 to 900 mPa·s and preferably indicates a value of 550 to 800 mPa·s. In a freeze-dried sodium alginate composition added with a salt, the viscosity usually indicates a value of 400 to 800 mPa·s and preferably indicates a value of 450 to 700 mPa·s.

The freeze-dried composition of the present invention is preferably kept in cold storage, preferably at 2 to 8° C. Preservation in cold storage suppresses the decomposition of the monovalent metal alginate and suppresses viscosity decrease at the supply of water. Consider the case where the freeze-dried composition of the present invention is kept in storage at 2 to 8° C. for 2 years and then is supplied with injection water so that the concentration is adjusted to 1% by mass. The viscosity decrease rate of that solution is usually less than 40%, preferably less than 30%, and further preferably less than 20%. The viscosity decrease rate can be extrapolated by accelerated test results, statistical processing, and the like.

The freeze-dried composition of the present invention can be used for medical purposes such as cartilage regeneration agent and cartilage disorder therapeutic agent, and can be dissolved using a solvent such as injection water and physiological saline to form a solution having a concentration and a viscosity suitable for the intended use. The solution can be used by impregnating a support such as a sponge with the solution. In addition, it is possible to use the solution gelated by addition of a cross-linking agent such as a solution of calcium chloride. Also, the gel can be used after freeze-drying. In addition, it is possible to take the freeze-dried composition of the present invention out of the vial and use the freeze-dried composition by, for example, crushing it and sprinkling it onto the diseased site.

The freeze-dried composition in the present invention includes a freeze-dried composition, a freeze-dried preparation, a freeze-dried body, a freeze-dried product, and the like.

Next, a preferable method of producing a freeze-dried composition of the present invention is described.

In other words, it is preferable to produce by a method of freeze-drying an aqueous solution formed by dissolving (a) a monovalent metal alginate and (b) a salt selected from a monovalent metal salt and an ammonium salt.

To be more specific, an aqueous solution is prepared by dissolving at least the component (a) and the component (b) into injection water. Here, it is preferable that the concentration of the monovalent metal alginate being the component (a) be 0.2 to 3% by mass and preferably about 0.3 to 2% by mass. The salt being the component (b) is recommended to be used in such an amount that the mass ratio of the component (a)/the component (b) is 100/70 to 100/10 and more preferably 100/60 to 100/30 relative to the component (a) used. Although the component (a) and the component (b) can be added into water in any order, it is preferable to add in the order of the component (a) and the component (b). Dissolution is usually performed at room temperature, but in some cases the solution may be heated or cooled. In the dissolution, any type of stirrer may be used.

In the present invention, the viscosity (20° C.) of the aqueous solution into which at least the component (a) and the component (b) are dissolved is preferably 40 to 800 mPa·s. Here, as the viscosity of the aqueous solution, it is possible to use a value measured at 20° C. by use of a two-axis cylindrical metal cup in RheoStress RS600 (manufactured by Thermo Haake GmbH).

After dissolution, undissolved matter may be removed by filtration of the aqueous solution as necessary. Here, it is preferable to perform aseptic filtration.

In the present invention, it is possible to fill any type of container with the aqueous solution into which at least the component (a) and the component (b) are dissolved and then to freeze-dry the aqueous solution. The container filled is preferably a vial and it is particularly preferable to fill a vial having a volume of 2 to 50 ml. It is preferable to fill a container which easily enables tight sealing after freeze-drying. The filling amount is about 1 to 90% and preferably about 10 to 50% of the volume of the vial.

The aqueous solution filled in any type of container is then frozen at any temperature. The freezing step is preferably performed taking a sufficiently long time within a temperature range between the temperature at which the aqueous solution is frozen and the temperature of −200° C. so that ice crystal grows uniformly and sufficiently. After that, freeze-drying is performed under reduced pressure, keeping the temperature settings within a range which maintains the ice crystal.

It is preferable to freeze the aqueous solution formed by dissolving at least the component (a) and the component (b) within a range from the freezing temperature to −50° C. and to perform first drying under reduced pressure within this temperature range. Subsequently, second drying is performed to reduce the water content to 3% by mass or less, preferably to 2% by mass or less, further preferably to 1% by mass or less, and most preferably to a level of substantially no water content. The water content of the freeze-dried composition can be measured in a usual manner, for example by the loss on drying method, the Karl Fischer method, and the like. If the freeze-dried composition has a moisture absorbing property, it is necessary to bear in mind that the measurement will not be affected by the absorption of moisture.

Here, the first drying refers to the process in which ice crystal disappears by sublimation of water molecules from ice, and the second drying refers to the process in which water bound to molecules sublimates. The water content at the end of the first drying (residual amount) depends on the freeze-dried matter and the amount thereof and is said to be about 15 to 30%.

Note that the temperature described in the freeze-drying conditions of the present invention means the shelf temperature of the freeze-dryer. The shelf temperature can usually be measured and monitored using a temperature sensor provided in the housing of the freeze-dryer. In addition, the freezing temperature described in the present invention means the shelf temperature set at the temperature at which the solution for the freeze-dried composition starts freezing.

The drying involves sublimation and removal of water contained in ice crystal produced due to freezing under a reduced pressure. The reduced pressure conditions here depend on the set shelf temperature, and may be a pressure of 0.0 to 50 Pa and preferably a pressure of 0.0 to 5 Pa. It is preferable to perform freeze-drying using a commercially available freeze-drying apparatus which enables reduced pressure drying under cooling.

In the present invention, the second drying can be performed under the same temperature condition as the first drying or under a temperature condition higher than the temperature of the first drying. In the case of a temperature condition higher than the first drying, there is a case where production time can be shortened. To be more specific, the second drying temperature is, but is not limited to, the range of −10° C. to 5° C., for example.

After the freeze-drying is finished, it is preferable to substitute the air in the vial with nitrogen gas, preferably dry nitrogen gas, and then to form a tightly sealed state using a cap. The cap is preferably made of rubber, in particular bromobutyl rubber. Note that it is possible to use a vial made of various commercially available materials such as a glass vial. In addition, it is possible to coat the inner wall of the vial with, for example, silicone.

The present invention further provides a suppressant viscosity decrease with the lapse of time for a freeze-dried monovalent metal alginate composition which includes a salt selected from a monovalent metal salt and an ammonium salt. In addition, the present invention provides a method of suppressing viscosity decrease with the lapse of time of a freeze-dried monovalent metal alginate composition which causes a freeze-dried monovalent metal alginate composition to contain a salt selected from a monovalent metal salt and an ammonium salt.

In these aspects, it is preferable to use the component (b) being a salt selected from a monovalent metal salt and an ammonium salt such that the mass ratio of the component (a)/the component (b) is within the range of 100/70 to 100/10 and more preferably within the range of 100/60 to 100/30 relative to the component (a) being a monovalent metal alginate. Thus, it is possible to suppress viscosity decrease with the lapse of time of the freeze-dried monovalent metal alginate composition.

EXAMPLES

Next, the present invention is described in further detail by showing examples. However, the present invention is not limited to these examples.

Example 1

Various freeze-dried sodium alginate compositions were prepared and their characteristics were measured and compared by the following method.
(1) Method of Preparing Aqueous Solution of Sodium Alginate Refined sodium alginate (purchased from KIMICA Corporation: purity (quantitative value determined) 98%: viscosity (1% by mass solution, 20° C.) 525 mPa·s: M/G ratio 1.2), sodium chloride (manufactured by Merck & Co., Inc.), and water (injection water: manufactured by Otsuka Pharmaceutical Co., Ltd.) were used.

Liquid agents A and B to be used described in Table 1 were prepared by stuffing a sterilized container having a volume of 1 to 2 L with refined sodium alginate alone or refined sodium alginate and sodium chloride together with injection water, followed by stirring and dissolution at room temperature.

Next, liquid agents A and B to be used were subjected to aseptic filtration using a 0.22 μm filter (manufactured by Millipore) inside a clean bench and were filled in a glass vial having a volume of 20 ml as a dry sodium alginate in an amount of 102 mg per vial.
(2) Freeze-Drying A glass vial filled with a sodium alginate aqueous solution was freeze-dried in the following conditions by use of a freeze-drying apparatus.

Freezing and drying conditions: cooling was performed to −40° C. for 270 minutes and complete freezing was performed at this temperature for 600 minutes of retention. After that, the temperature was cause to rise to −10° C. At this temperature, pressure was reduced so that the pressure inside the housing of the freeze-dryer was 3 Pa or less, followed by retention for about 120 hours to perform drying to make the water content about 2% by mass.

After the freeze-drying, the air of the vial was substituted with dry nitrogen gas and then a tightly sealed state was formed using a cap. The resultant was provided for the following test.

Table 1 shows the formulation, the drying temperature, and the like of the sodium alginate aqueous solution collectively.

TABLE 1

| No. | Formulation | Liquid Agent Used | Drying Temperature | Concentration of Liquid Agent |
|---|---|---|---|---|
| Example 1-3 | No Additives | A | −10° C. | Sodium Alginate 5.1 g/L |
| Example 1-1 | Added with NaCl 2.25 g/L | | | |
| Example 1-4 | No Additives | B | | |
| Example 1-2 | Added with NaCl 2.25 g/L | | | |

(3) Test Conditions

In the examples, the freeze-dried sodium alginate product was subjected to stress by being stored in a constant temperature and humidity room of 40° C. and 75% RH for 60 days in order to evaluate viscosity change with the lapse of time of sodium alginate.
(4) Analysis Method The change of viscosity with the lapse of time was investigated as follows: the viscosity at 20° C. was measured for 3 minutes by use of a two-axis cylindrical metal cup in RheoStress RS600 (manufactured by Thermo Haake GmbH); and the measurement value employed was the average during the interval between 1 minute after the start and until 2 minutes after the start. To be more specific, the freeze-dried sodium alginate products were removed as time passed. Injection water was supplied so that the concentration of sodium alginate was 1% by mass, followed by measurement of viscosity.
(5) Results FIG. 1 shows the obtained results.

Comparison of Examples 1-1 and 1-2, and Examples 1-3 and 1-4 in FIG. 1 shows that the initial viscosities of the examples added with sodium chloride (1-1 and 1-2) (storage period is 0 days) tends to be low compared to the examples not added with sodium chloride (1-3 and 1-4). This phenomenon is an apparent decrease caused by sodium chloride added and is not attributed to quality degradation. Viscosity decrease with the lapse of time is more gentle for the examples (1-1 and 1-2) compared to the examples (1-3 and 1-4). When the storage period exceeds 30 days, the viscosities of the pairs reverse. When the storage period exceeds 60 days, it can be seen that the difference in viscosity between the pairs is large. This indicates that the monovalent metal salt being sodium chloride can suppress viscosity decrease with the lapse of time of the monovalent metal alginate being sodium alginate. The viscosity decrease rate (change rate from the initial value) at day 30 has decreased by about 30% for the examples (1-3 and 1-4), whereas about 10% for the examples (1-1 and 1-2). It was observed that addition of sodium chloride further suppressed viscosity decrease.

Simultaneously, an experiment of changing the concentration of liquid agent (10 mg/L) and changing the size of the vial (vial having a volume of 50 ml) was carried out. However, neither the change in the concentration of liquid agent nor the change in the size of the vial (change in the filling amount) affected stability.

What is claimed is:

1. A freeze-dried composition consisting of (a) a monovalent metal alginate, (b) sodium chloride, and (c) water, wherein the water content is 3% by mass or less, and wherein the monovalent metal alginate has a weight average molecular weight of 500,000 to 5,000,000 obtained by gel filtration chromatography, and a mass ratio of the component (a)/the component (b) is 100/70 to 100/10.

2. The freeze-dried composition according to claim 1, which is a freeze-dried aqueous solution formed by dissolving at least the components (a) and (b).

3. An in-vial freeze-dried composition formed by storing the freeze-dried composition according to claim 1.

4. The in-vial freeze-dried. composition according to claim 3, wherein a volume of a vial is 2 to 50 ml.

5. The in-vial. freeze-dried composition according to claim 3, wherein air in the vial is substituted with nitrogen gas.

6. The freeze-dried composition according to claim 1, the monovalent metal alginate having an endotoxin value g measured by the endotoxin test conforming to the Japanese Pharmacopoeia of less than 100 EU/g.

7. The freeze-dried composition according to claim 1, wherein the monovalent metal alginate is a sodium alginate.

8. The freeze-dried composition according to claim 1, wherein a water content is 2% by mass or less.

9. A method of producing a freeze-dried composition according to claim 6, comprising the steps of freezing an aqueous solution formed by dissolving at least the component (a) and the component (b), performing a first drying under reduced pressure within a temperature range where the freezing is kept, and then performing a second drying to reduce a water content to 3% by mass or less.

10. The freeze-dried composition according to claim 1, wherein the composition is suitable for use in the treatment of cartilage regeneration or cartilage disorder.

11. The freeze-dried composition, according to claim 1, wherein the M/G ratio of the monovalent metal alginate is 0.4 to 2.0.

12. The freeze-dried composition according to claim 1, where the freeze-dried composition is kept in storage at 2 to 8° C. for 2 years and then is supplied with injection water so that the concentration is adjusted to 1% by mass, the viscosity decrease rate of that solution is less than 40%.

13. The freeze-dried composition according to claim 1, wherein the composition is a freeze-dried preparation.

14. The freeze-dried composition according to claim 1, wherein the monovalent metal alginate has a weight average molecular weight of 650,000 to 5,000,000 obtained by gel filtration chromatography.

15. The freeze-dried composition according to claim 1, wherein the monovalent metal alginate has a weight average molecular weight of 800,000 to 3,000,000 obtained by gel filtration chromatography.

16. The freeze-dried composition according to claim 11, wherein the M/G ratio of the monovalent metal alginate is 0.6 to 1.8.

17. The freeze-dried composition according to claim 11, wherein the MIG ratio of the monovalent metal alginate is 0.8 to 1.6.

18. The freeze-dried composition according to claim 6, wherein the monovalent metal alginate having an endotoxin value measured by the endotoxin test conforming to the Japanese Pharmacopoeia is less than 75 EU/g.

19. The freeze-dried composition according to claim 6, wherein the monovalent metal alginate having an endotoxin value measured by the endotoxin test conforming to the Japanese Pharmacopoeia is less than 50 EU/g.

20. The freeze-dried composition according to claim 1, wherein the water content is measured by a loss on drying method.

21. The freeze-dried composition according to claim 1, wherein mass ratio of he component (a)/the component (b) is 100/70 to 100/44.

* * * * *